US008911469B2

(12) United States Patent
Raheman

(10) Patent No.: US 8,911,469 B2
(45) Date of Patent: Dec. 16, 2014

(54) METHODS AND APPARATUS FOR OPTIMAL REMOTE ISCHEMIC PRECONDITIONING (ORIP) FOR PREVENTING ISCHEMIA-REPERFUSION INJURIES TO ORGANS

(75) Inventor: Fazal Raheman, Dubai (AE)

(73) Assignee: NeoCardium, Limited, St Leonard on Sea, East Sussex (GB)

( * ) Notice: Subject to any disclaimer, the term of this patent is extended or adjusted under 35 U.S.C. 154(b) by 434 days.

(21) Appl. No.: 12/898,259

(22) Filed: Oct. 5, 2010

(65) Prior Publication Data

US 2011/0238107 A1 Sep. 29, 2011

Related U.S. Application Data

(60) Provisional application No. 61/317,294, filed on Mar. 25, 2010.

(51) Int. Cl.
*A61B 17/00* (2006.01)

(52) U.S. Cl.
USPC ............ 606/202; 606/203; 600/483; 600/485

(58) Field of Classification Search
None
See application file for complete search history.

(56) References Cited

U.S. PATENT DOCUMENTS

| 4,773,419 | A | 9/1988 | Tountas |
| 5,571,075 | A | 11/1996 | Bullard |
| 6,962,599 | B2 | 11/2005 | Hui |
| 7,048,702 | B2 | 5/2006 | Hui |
| 7,338,410 | B2 | 3/2008 | Dardik |
| 7,341,562 | B2 * | 3/2008 | Pless et al. .................... 600/504 |
| 7,774,057 | B2 | 8/2010 | Pastore |
| 2003/0233118 | A1 | 12/2003 | Hui |
| 2004/0255956 | A1 | 12/2004 | Vinten-Johansen et al. |
| 2006/0100639 | A1 | 5/2006 | Levin et al. |
| 2006/0287684 | A1 | 12/2006 | Baynham et al. |
| 2007/0150005 | A1 | 6/2007 | Sih et al. |

(Continued)

FOREIGN PATENT DOCUMENTS

GB 2434536 A 8/2007

OTHER PUBLICATIONS

Kharbanda, R.K., Transient Limb Ischemia Induces Remote Ischemic Preconditioning In Vivo, Circulation Journal of the American Heart Association, American Heart Association, vol. 106, pp. 2881-2883 (2002).*

(Continued)

*Primary Examiner* — Katherine Dowe
*Assistant Examiner* — Sidharth Kapoor

(57) ABSTRACT

Ischemia-reperfusion injury commonly results from any surgical procedure requiring stopping of blood supply to an organ followed by reperfusion such as in heart bypass, angioplasty or organ transplant. The invention discloses a method to harness the innate power of repetitive transient ischemia in protecting organs against imminent ischemia-reperfusion, or any patho-physiological insults. This method of optimal remote ischemic preconditioning (ORIP) comprises of utilizing a pair of programmable pneumatic cuffs that inflate/deflate alternately occluding blood circulation to each of the limbs for pre-defined time intervals. The apparatus delivers maximal ORIP dose in shortest possible time either as an EMS procedure during patient transportation to hospital, as elective pre-surgery treatment, or in critical care for preventing multiple-organ-dysfunction-syndrome. ORIP can be self-administered and remotely monitored by clinician especially in chronic patients for homeostasis of malfunctioning target organs. ORIP may also be deployed as adjunct in angioplasty, gene/stem cell heart repair therapies.

8 Claims, 8 Drawing Sheets

ORIP EMS / P3 / CC Web Architecture In An Acute Treatment Scenario

Ischemic Zones In Different Embodiments Of ORIP

(56) References Cited

U.S. PATENT DOCUMENTS

| | | |
|---|---|---|
| 2008/0033307 A1 | 2/2008 | Baudoin et al. |
| 2008/0139949 A1 | 6/2008 | Caldarone et al. |
| 2008/0177156 A1 | 7/2008 | Zhang et al. |
| 2009/0137884 A1 | 5/2009 | Naghavi et al. |
| 2009/0264774 A1 | 10/2009 | Kondo et al. |
| 2009/0287069 A1 | 11/2009 | Naghavi et al. |
| 2010/0105993 A1 | 4/2010 | Naghavi et al. |
| 2010/0160799 A1 | 6/2010 | Caldarone et al. |
| 2010/0185220 A1 | 7/2010 | Naghavi et al. |
| 2010/0324429 A1 | 12/2010 | Leschinsky |

OTHER PUBLICATIONS

Kloner, R.A., Clinical Application of Remote Ischemic Preconditioning, Circulation Journal of the American Heart Association, American Heart Association, vol. 119, pp. 776-778 (2009).*

Stavros, P.L., et al., Transietn Limb Ischemia Induces Remote Preconditioning and Remote Postconditioning in Humans by a K.sub. ATP. Channel-Depednent Mechanism, Circulation Journal of the American Heart Association, American Heart Association, vol. 116, pp. 1386-1395 (2007).*

* cited by examiner

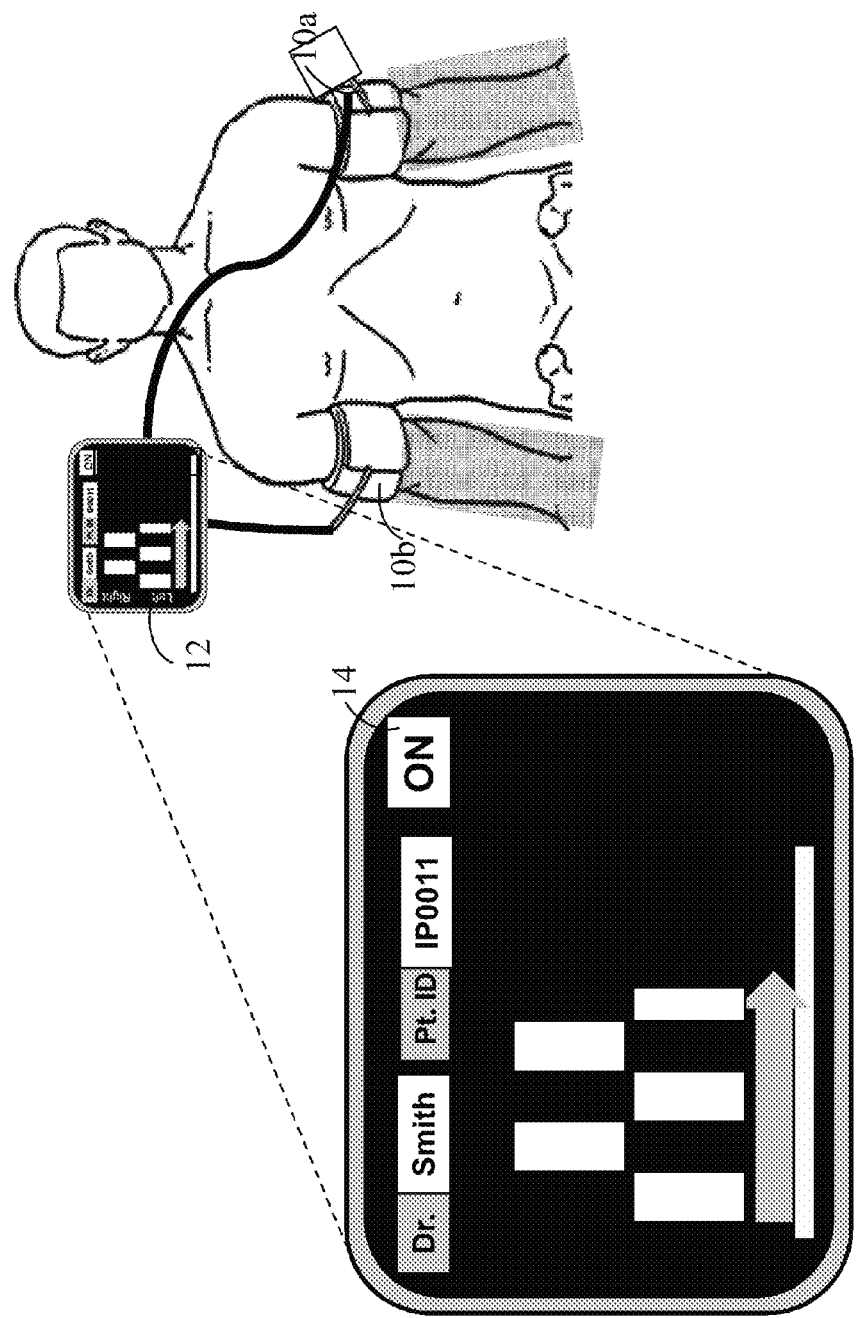
FIG. 1. ORIP Treatment Session In Progress

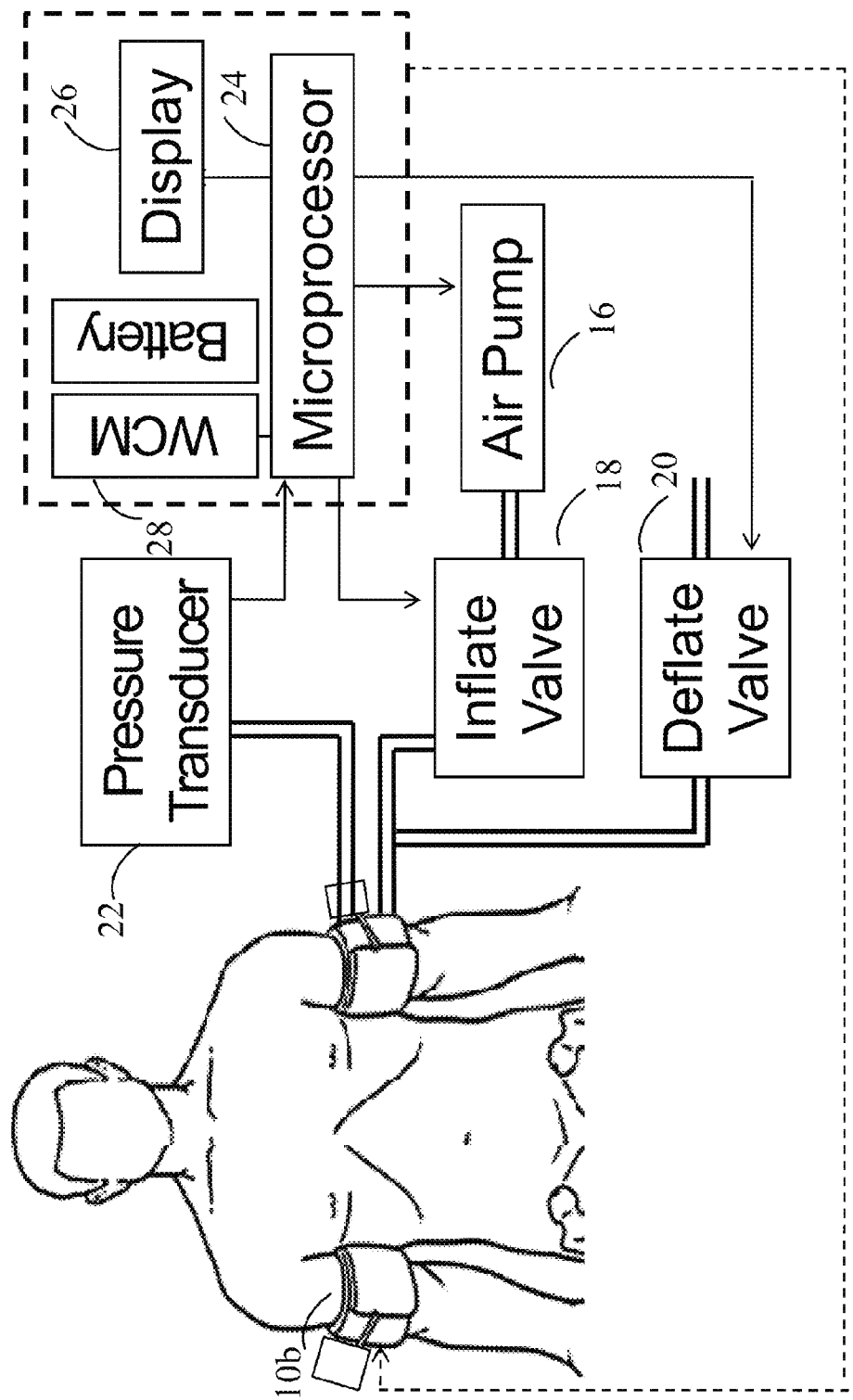
FIG. 2. Block Diagram - Elements of ORIP & Each Pneumatic Cuff

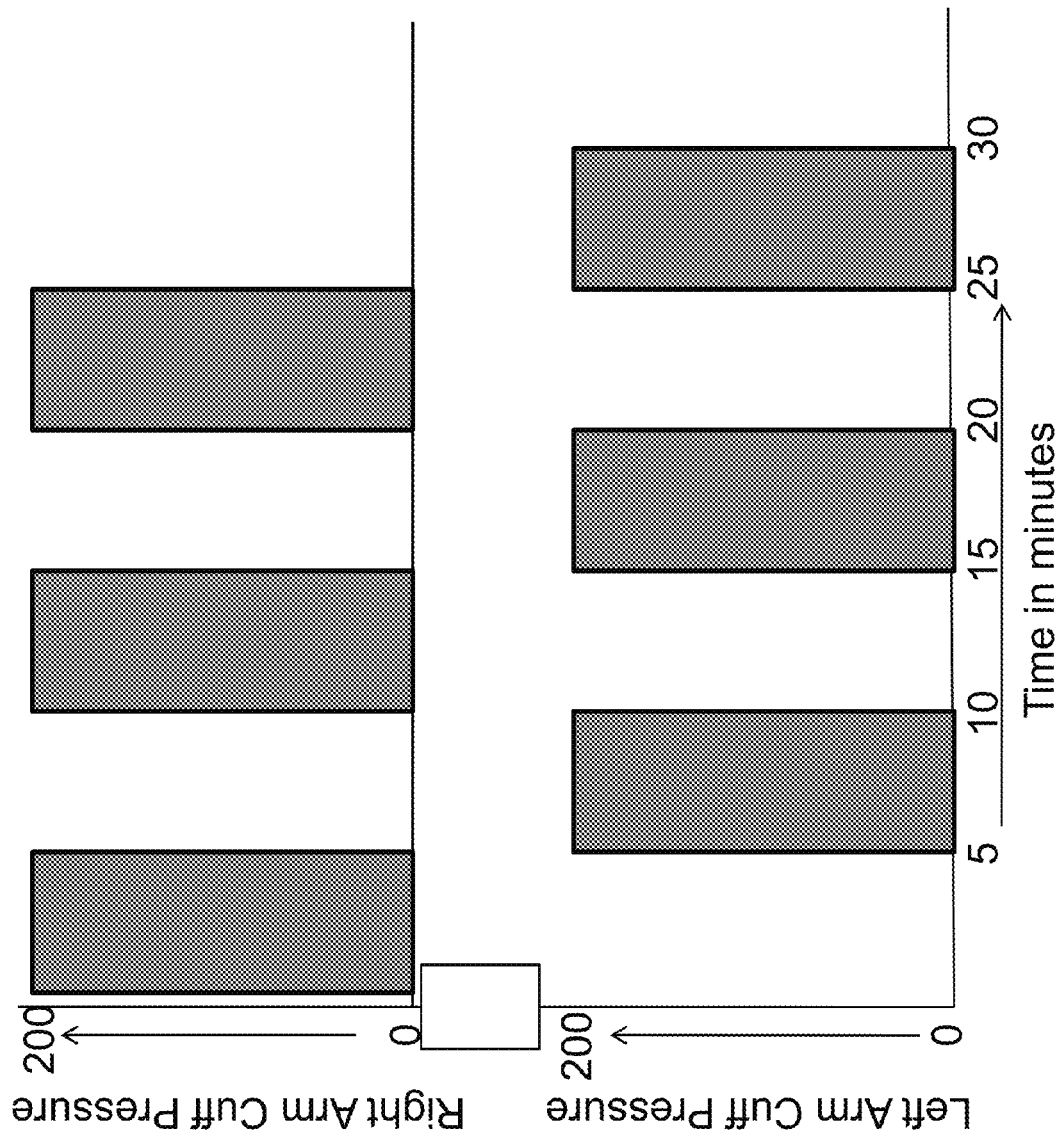
FIG. 3. Sequence of Equal & Alternating Inflation/Deflation Cycles In Limbs

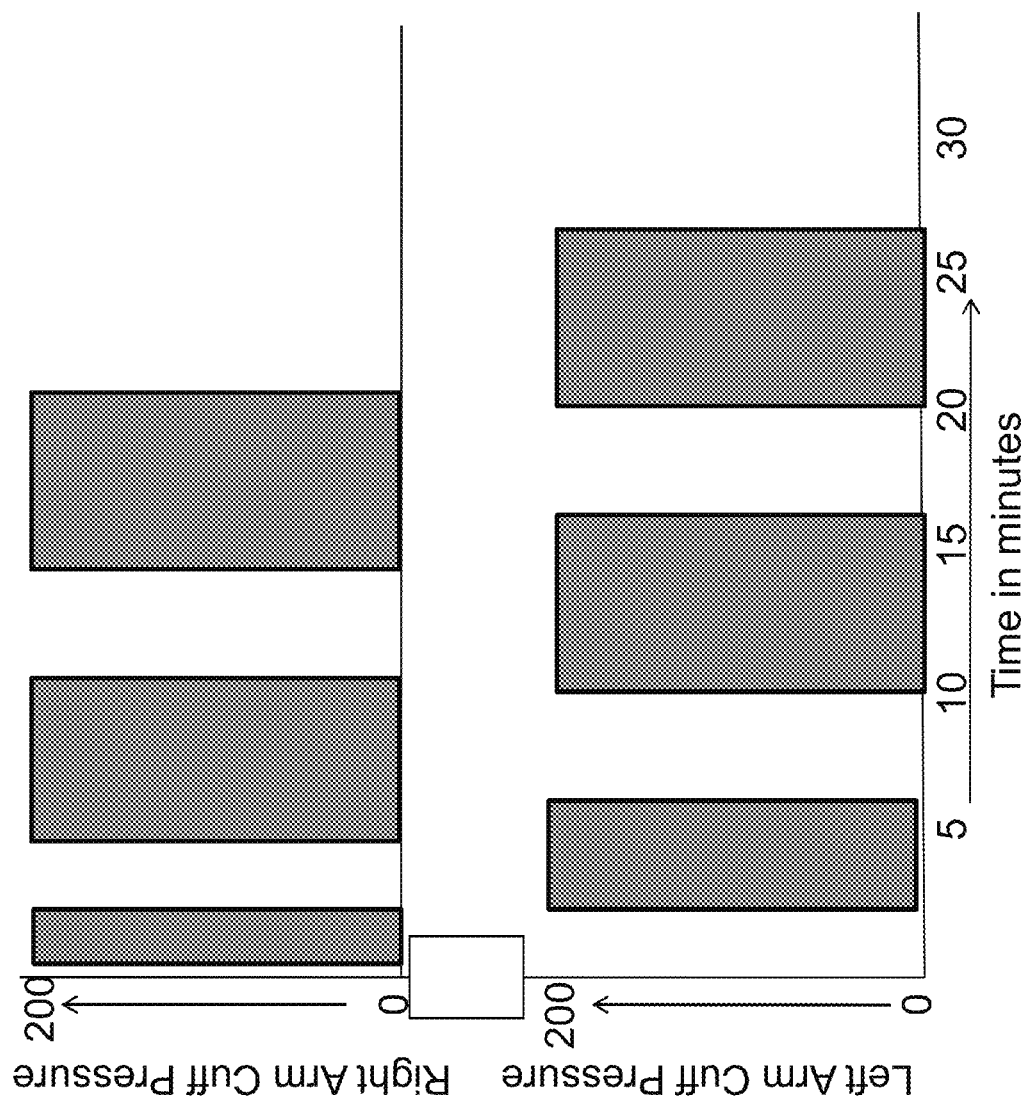
FIG. 4. Sequence of Escalating Timing of Inflation/Deflation Cycles In Limbs

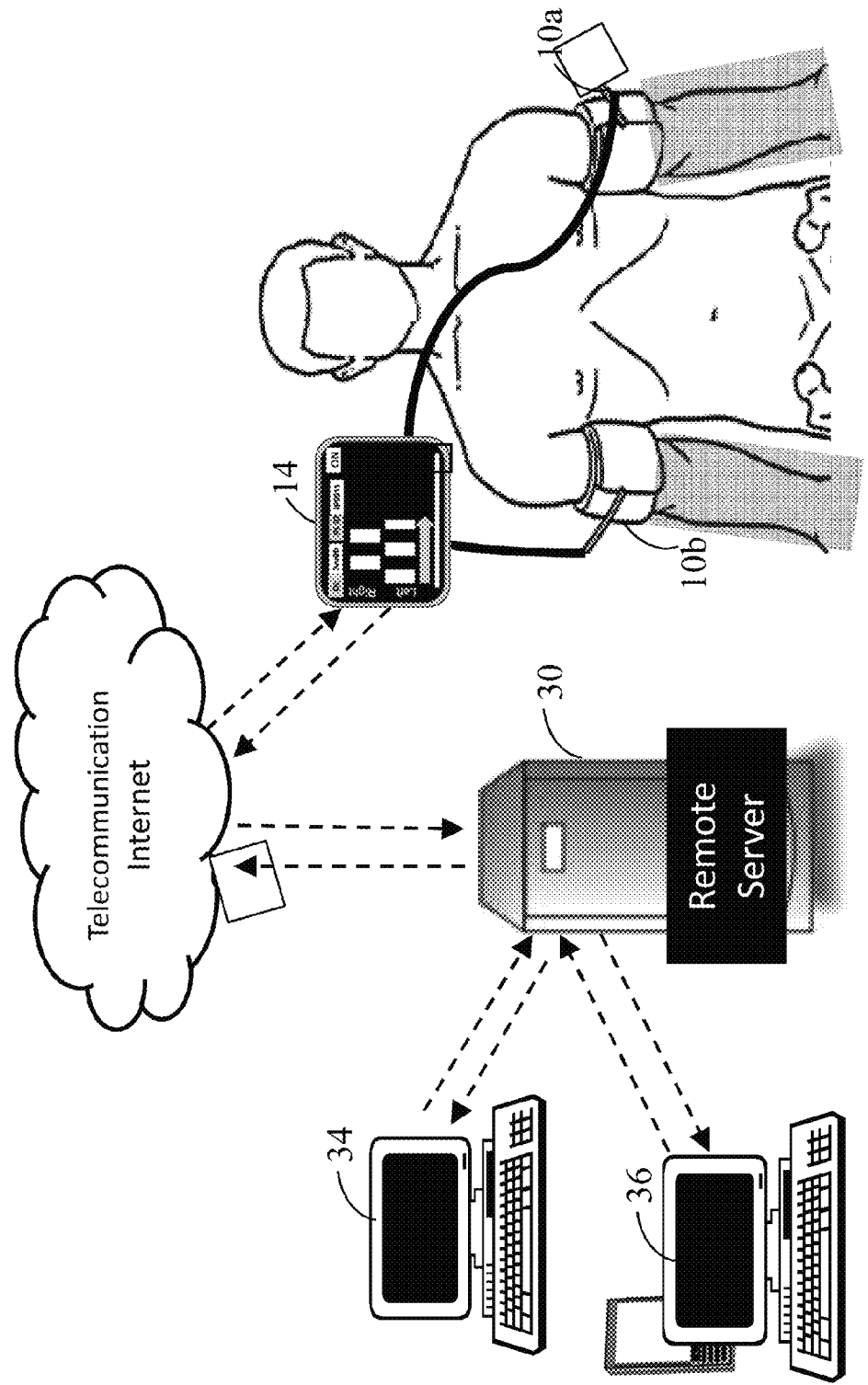
FIG. 5. ORIP EMS / P3 / CC Web Architecture In An Acute Treatment Scenario

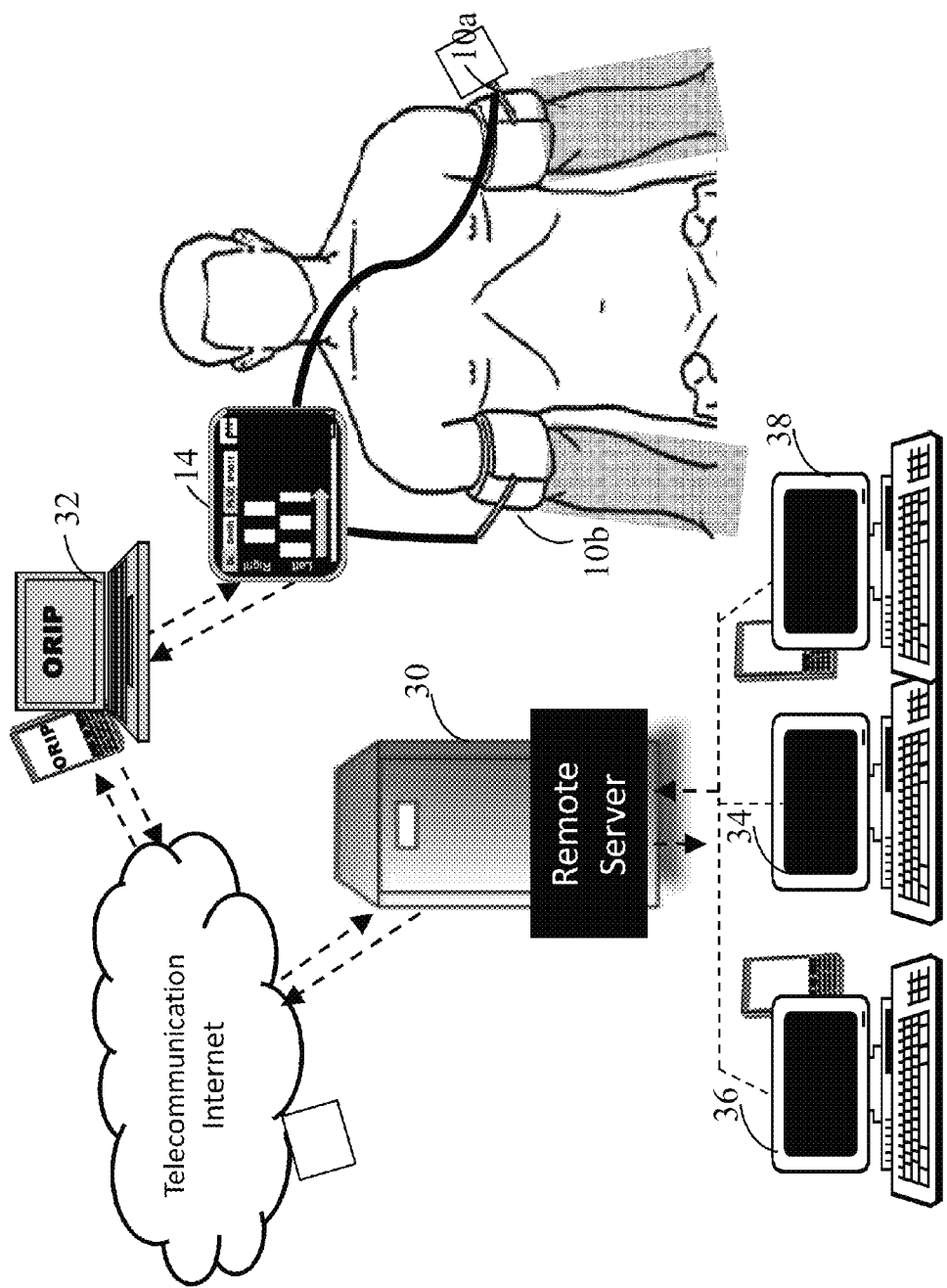
FIG. 6. ORIP Apparatus With RF Module

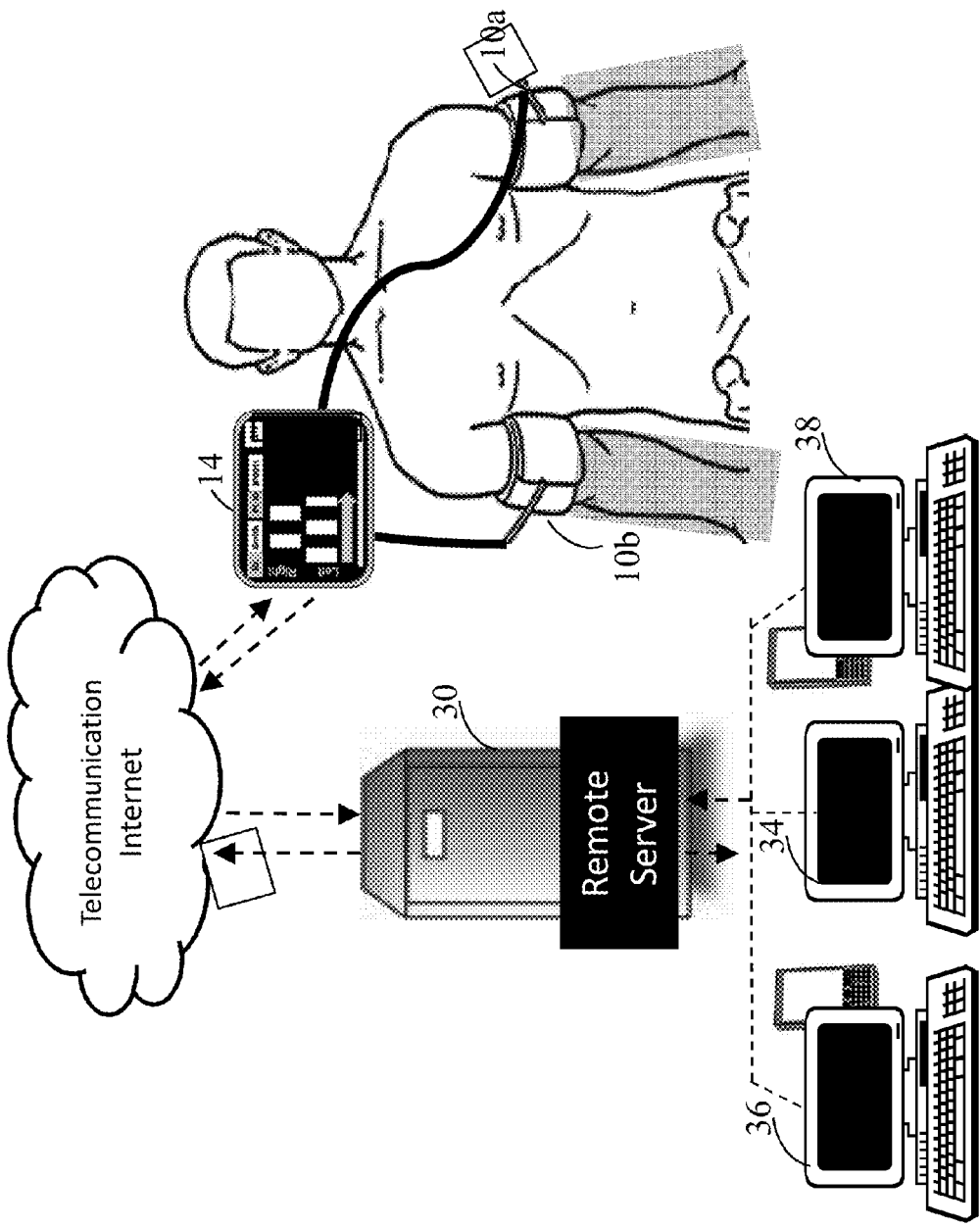
FIG. 7. ORIP Web Architecture In Chronic/Sub-acute Treatment Scenario

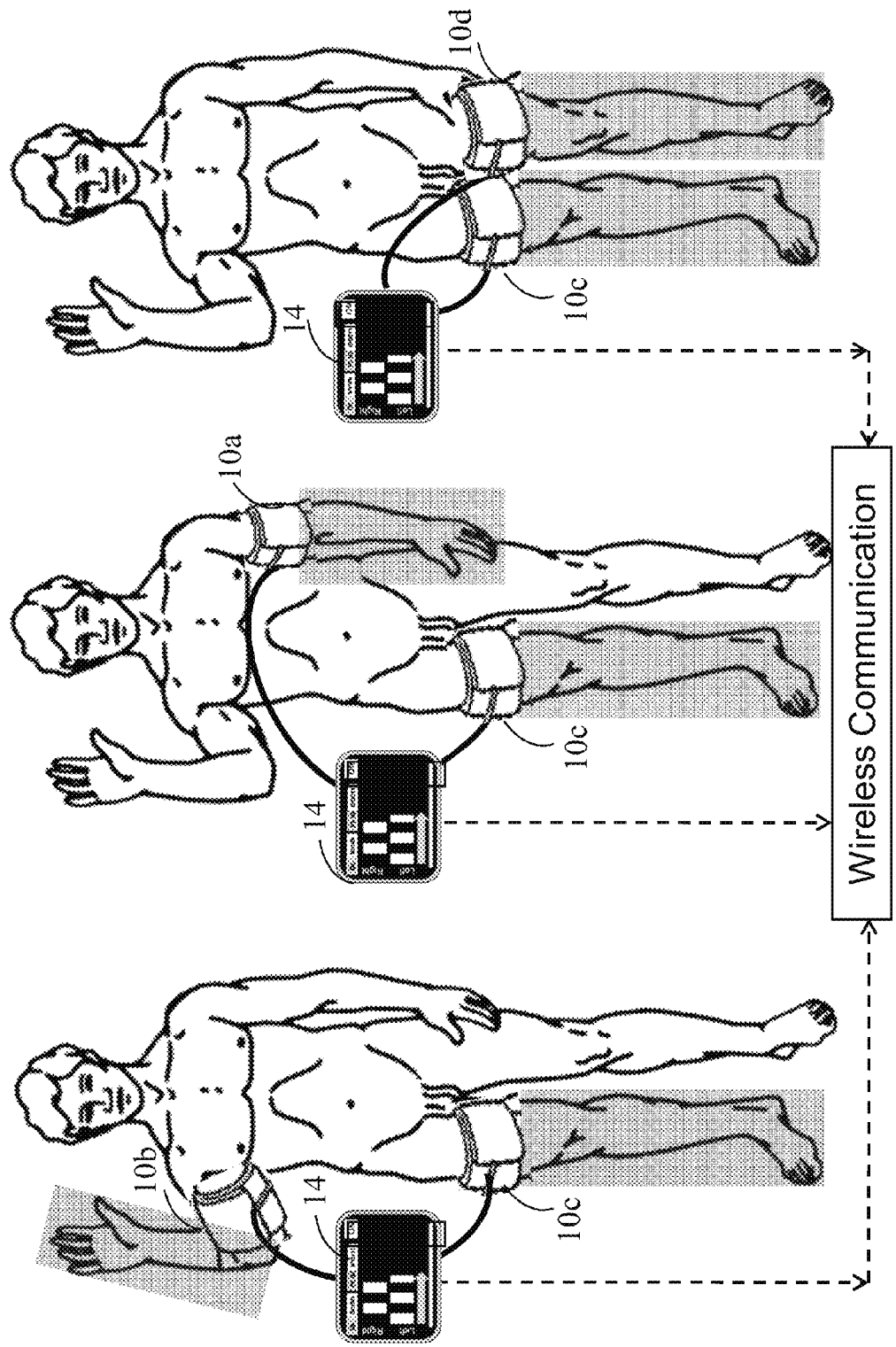
FIG. 8. Ischemic Zones In Different Embodiments Of ORIP

METHODS AND APPARATUS FOR OPTIMAL REMOTE ISCHEMIC PRECONDITIONING (ORIP) FOR PREVENTING ISCHEMIA-REPERFUSION INJURIES TO ORGANS

This invention claims the benefit of U.S. Provisional Application No. 61/317,294 filed on Mar. 25, 2010

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention relates generally to transiently and repeatedly auto inflating pneumatic cuffs for inducing limb ischemia distal to its site of occlusion and preconditioning the entire human body to subsequent ischemic and other physiological and pathological insults. More particularly it is a method of remote ischemic preconditioning by occluding limb circulation utilizing a pair of pneumatic cuffs that inflate and deflate alternately for a pre-specified time to induce optimal limb ischemia sufficient for inducing system-wide ischemic preconditioning for protecting the organs from injury resulting from sustained ischemic, physiological or pathological insults.

BACKGROUND OF THE INVENTION

In a pending U.S. patent application bearing Ser. No. 12/545,172, this inventor disclosed a wearable personal communication device based method of non-pharmaceutical prescription that administers, monitors, measures and motivates a therapeutic lifestyle regimen for improving prevention, treatment and prognosis of chronic diseases. The '668 disclosure termed Rx-Zero teaches not only the prevention component by eliminating the need for pharmaceutical interventions, but also includes the therapy component after the chronic disease has actually been diagnosed. In the former the disease onset is prevented before it sets in, while in the later situation it targets the lifelong drug usage to minimal or zero by deploying the lifestyle changes as the first line of treatment, and prescription drugs only to supplement and support the first line of treatment.

Although the '668 Rx-Zero disclosure measured and monitored the therapeutic dose of physical activity prescribed and its impact on health in general it did not consider other parameters that may be implicated in optimizing the doses of physical activity to maximize the gains of revascularization interventions and minimize the post procedure restenosis complications in everyday interventional cardiology practice. To fill that gap this inventor, in another application, disclosed a method and apparatus that enables prescription, administration and monitoring compliance of a measured therapeutic or rehabilitative optimal myocardial stress induction (OMSI) regimen for complimenting a coronary revascularization intervention to prevent/reduce the post-procedure restenosis risk. In continuation of the concept of non-pharmacological intervention for management of morbidities the instant invention exploits another naturally occurring phenomenon of remote ischemic preconditioning for preventing subsequent ischemia-reperfusion injury, or improving vascular functions of patient with chronic cardiovascular disease. The instant invention discloses an apparatus to harness the innate power of transient ischemia in preparing the body for better defense against ischemic, ischemia-reperfusion, or any other physiological or pathological insults to organs.

Ischemia-reperfusion injuries are implicated in a large array of pathological conditions such as myocardial infarction, cerebral stroke, and hepatic, renal or lung transplant, etc. Unfortunately such ischemia-reperfusion injuries are still considered as an inevitable price the patient has to pay for the surgical intervention. Most patients who undergo revascularization of blocked coronary arteries end up with larger size infarct (dead myocardium) then that caused by the blockage itself, merely because of the revascularization procedure undertaken to open up the blockages and salvage the myocardium. It is a paradox that the procedure that aims to perfuse and salvage the myocardium kills more of it in the process. Moreover, almost all of the patients undergoing balloon catheterization face long term effects of ischemia-reperfusion injury caused during ballooning and stenting. Such long term effects include increased risk of restenosis and future cardiovascular events.

While the benefit of an improved perfusion of the myocardium is certainly desirable, nevertheless the cost of an increased infarct size is indeed a very high price to pay. The actual annual cost of ischemia-reperfusion injury to mankind therefore is humongous and incalculable considering millions of such high reperfusion injury risk procedures are performed globally on a daily basis. While lethal reperfusion injury remains the next major target for the treatment of patients with acute myocardial infarction and coronary revascularization, many other surgical settings such as organ transplant, protracted procedures requiring clamping of blood supply to an organ remain ridden with the ischemia-reperfusion injury problem. There are no current solutions on the market to address this huge problem.

Transient tissue hypoxia/ischemia is one of the most potent physiological triggers of systemic protection against subsequent ischemia-reperfusion related damage to the organs. It is the most potent innate mechanism of protection that can be induced in our tissues. Yet ischemia-reperfusion injury to organs remains the most commonly acknowledged risk of surgical intervention in the practice of modern medicine. In their 1986 seminal paper Murray et al for the first time reported this natural ischemic pre-conditioning phenomenon (Murray C E, et al. Circulation 1986; 74 (5): 1124-36). Subsequently it was demonstrated in a canine model that brief episodes of ischemia in one myocardial vascular bed, protects remote virgin myocardium from a sustained coronary artery occlusion feeding another vascular bed implying that preconditioning may be mediated by factors activated, produced, or transported throughout the heart during brief ischemia/reperfusion (Przyklenk K, et al. Circulation. 1993; 87(3):893-9). However, only in the preceding few years there has been a flurry of reports discovering that the ischemic preconditioning can be easily induced systemically with a remote stimulus, without having to access the target organ itself (Ali Z A et al. Circulation. 2007 Sep. 11; 116(11 Suppl: I98-105; Venugopal V et al. Eur. J. Cardiothorac. Surg. 2009; 35:977-987; Kharbanda R K et al. The Lancet, 2009; Vol 374: 9700, 1557-1565, 31). The knowledge that transient intermittent ischemia in limbs can remotely induce ischemic preconditioning in the entire body is fast changing the landscape of ischemia-reperfusion injury.

Recent clinical studies emphasize that lethal reperfusion injury represents a large amount of the overall myocardial damage after acute myocardial infarction, and have shown that ischemic preconditioning substantially reduces infarct size, and that this tissue destruction during surgical procedures such as coronary revascularization can be prevented by a timely intervention with remote ischemic preconditioning (Ovize M & Bonnefoy E. The Lancet, 2010; Vol 375:9716, 699-700, 27). Although ischemic preconditioning has been largely studied more extensively in the context of myocardial damage, there are reports of similar beneficial effects on almost any organ of the body.

For example Dembinski A et al showed that ischemic preconditioning, applied prior to ischemia-reperfusion-induced pancreatitis, strongly reduces the severity of acute pancreatitis via reduction in plasma lipase activity and a decrease in plasma concentration of pro-inflammatory interleukin-18, and increase in plasma concentration of anti-inflammatory interleukin-10, improvement in pancreatic blood flow and increased expression of PDGF-A and VEGF (Dembinski et al. Physiol Pharmacol 2006; 57(1):39-58). Nikeghbalian et al subsequently showed the ischemic preconditioning of liver protected pancreas from ischemia-reperfusion injury (Nikeghbalian S, et al. Saudi J Kidney Dis Transpl 2009; 20:1010-4).

Botker et al very recently reported a randomized study in which arm ischemia (induced by four cycles of alternating 5-min inflation and 5-min deflation of a standard upper-arm blood-pressure cuff) significantly increased myocardial salvage in 142 patients with ST-elevation acute myocardial infarction (STEM) (Botker H E, et al. The Lancet, 2010; Vol 375:9716, 727-734, 27).

Remote ischemic preconditioning, as is emerging today, may appear easy to deliver through a straightforward procedure such as intermittent ischemia of the upper or lower limb, induced by inflating and holding a blood-pressure cuff above the patient's systolic blood pressure. It has no known adverse risks and in the published clinical studies the technique is executed using a manual auscultatory sphygmomanometer. The ability to use the manually inflating blood pressure cuff, albeit with obvious inconvenience of a continuous hour long doctor/nurse-in-attendance procedure, is predicted as the downfall of this otherwise low-tech technique. Its non-pharmacological nature is also feared to preclude sponsorship from the pharmaceutical industry.

The currently available automatic sphygmomanometers use a self-inflating cuff to exert controlled counter-pressure on the vasculature of a patient. In typical automatic sphygmomanometric devices, the cuff deflation operation is accomplished in equal decrements, usually about 8 mm Hg per step. They are not designed to hold pressure for an extended duration and cannot cycle between ischemic and reperfusion durations as may be required when remote ischemic preconditioning is performed on patients. As such, only manually inflatable blood pressure measuring systems can be used. But such systems require the presence of a medical professional throughout the procedure that may take over an hour to complete. Remote ischemic preconditioning protocols may also vary extensively from patient to patient or even from treatment to treatment for a given patient, which may cause confusion among those that administer the treatment. Such procedure is therefore impractical in an emergency when the patient is being transferred to the hospital for treatment. It is also is impractical for a cardiologist to spend an hour on the procedure when the actual angioplasty may take even lesser time. It is also impractical if the ischemic preconditioning is prescribed to a home-based ambulatory patient on a regular basis.

Therefore there is urgent need to solve all of these problems and accomplish the entire procedure of prescribing, administering, monitoring and measuring and optimizing the ischemic preconditioning regimen with a single touch use friendly device requiring very little of the physician time or with his remote supervision of the treatment protocol.

DESCRIPTION OF THE PRIOR ART

The prior art in the area of various types of sphygmomanometers is quite extensive. However, as far as using pneumatic cuffs to occlude blood flow to a particular organ is concerned, the prior art is limited. There exist systems for occluding blood flow through a patient's limb during surgery, so as to create a bloodless operating field such as Pressure-Responsive Tourniquet described by Clark in a PCT publication WO 83/00995. The Clark method maintains cuff pressure at a set point above systolic pressure, but lacks any controls for releasing the cuff and re-inflating the cuff as required in ischemic preconditioning.

Pneumatic cuffs have also been used to produce external counter-pulsation blood flow in a patient as disclosed by Hui in U.S. Pat. No. 7,314,478. In external counter-pulsation treatment, a series of pneumatic cuffs are wrapped about a subject's limbs and are inflated and deflated in a manner that creates a pressure wave which is believed to increase the blood flow to the subject's heart. The inflation and deflation cycles are timed to the subject's heart beat, instead of longer durations typically required in ischemic preconditioning. Therefore external counter-pulsation treatment systems are also inadequate.

Recently Caldarone et al US Pub. No. 20080139949, and more recently Morteza et al US Pub No. 20090287069 disclosed systems for performing remote ischemic preconditioning. While Caldarone invention is designed for ischemic preconditioning for acute situations such as treatment prior to an elective medical procedure or during patient transfer for an emergency procedure, the Morteza disclosure is designed for treatment of chronic conditions particularly hypertension.

Morteza disclosure does not talk about self-administration of the ischemic preconditioning treatment. It is obvious that a patient with chronic hypertension cannot visit the clinic several times in a week. It is therefore imperative that the device includes the capability of user friendly self-administration on one hand and close monitoring by the clinician on the other. Since this is a therapeutic procedure it has to be prescribed by a licensed clinician and closely monitored by the prescribing clinician. The practical application of any type of remote ischemic preconditioning therefore requires that the prescribing clinician is in control and direct supervision of any particular regimen being administered to the patient whether in acute conditions or in chronic conditions. This is neither possible in Calderone nor in Morteza. Moreover, both Caldarone and Morteza do not describe an apparatus that implements an ischemic preconditioning regimen in the shortest possible time with maximal therapeutic effect and minimal discomfort to the patient. Recently Naghavi (US Patent Pub No. 20100105993) disclosed another apparatus that depends on "measuring markers of one or more ischemia, blood flow, and metabolism" and then "adjusting the ischemia based on the sensed results."

It is now well established that age, gender and the presence of disease states, such as hypertension, diabetes, metabolic syndrome, atherosclerosis and hyperlipidaemia, can attenuate the protective effect of remote ischemic preconditioning (Ferdinandy et al., Pharmacol Rev. 59, 418-458, 2007). However, Tsang et al demonstrated that the beneficial protective effect of remote ischemic preconditioning may still be possible in diabetes with a stronger stimulus and suggested a kind dose response effect (Tsang et al., Diabetes 54, 2360-2364, 2005a). In the presence of such co-morbid conditions, Calderone or Morteza methods may take almost two hours for delivering equivalent preconditioning dose, which is not only impractical in emergency situations or in operation room, or in ICU or even in self-administration of ambulatory patients.

Accordingly there is a need for device that can administer the Optimal Remote Ischemic Preconditioning (ORIP) to create a larger ischemic zone without much patient discomfort in minimum possible time as an Emergency Medical Service (EMS) by the paramedic during the transport of the patient to the hospital, or in a typical pre-procedure preparation of a patient in a hospital before an elective procedure is undertaken by the clinician or in a patient who is at very high risk of developing organ failure. There is also a need for a suitable apparatus that can deliver higher remote ischemic preconditioning stimuli/doses to patients with known ischemic preconditioning attenuating co-morbidities, such as diabetes, without making the procedure lengthy, tedious, uncomfortable and impractical. There is also a need for ORIP method as a suitable apparatus for long term Chronic Medical Service (CMS), or for sub-acute treatment of certain clinical conditions in which the ORIP treatment can be self administered comfortably without physical presence of a physician and yet can be under direct remote supervision of the physician, and which may also provide remote interactivity with patient and the physician.

SUMMARY OF THE INVENTION

The present invention addresses the foregoing need for a method and apparatus for prescribing, administering and monitoring optimal remote ischemic preconditioning for the purpose of preventing acute ischemia-reperfusion injuries during an impending surgery or some such situation of prolonged ischemia preceding reperfusion, or acute or chronic physiological or pathological insults to organs. Accordingly, there is a need for a versatile invention as summarized herein in some detail. Consequently, it is an advantage of the invention that it objectively administers the prescribed remote ischemic preconditioning dose optimally with a single touch and in half the time of any manual or automatic procedure known to the prior art without significant pain or discomfort to the patient. It is further advantage of the method that it creates at least two ischemic-reperfusion zones in two different remote organs of the patient in a single dosing session thereby creating a much larger ischemic preconditioning space resulting in a much stronger protective response to any subsequent ischemia-reperfusion injury.

It is therefore an object of the present invention to provide an entirely new method of prescribing a non-pharmacological prophylactic and therapeutic ORIP treatment regimen for preventing ischemia-reperfusion injury in an acute EMS setting as well as in chronic CMS setting for treating chronic diseases as by means of a user friendly portable device that administers, monitors, measures and ensures compliance of the ORIP treatment regimen with the eventual goal of minimizing the consequences of ischemia-reperfusion related vascular morbidities.

It is also an object of the present invention to deliver the maximal dose of ischemia in shortest possible time without patient discomfort for inducing optimal system wide ischemic preconditioning for increasing the threshold of organs to withstand ischemia-reperfusion in particular, and all known physiological and pathological insults in general.

It is also an object of the present invention to place ORIP dosing protocol under the direct control of the clinician who can prescribe and monitor the treatment regimen remotely in real time. It is also another object of the invention to allow the home-based self-administration of the ORIP treatment by a chronically ill ambulatory patient under continuous monitoring and surveillance of the prescribing clinician as a chronic medical service (CMS). It is yet another object to make the method and apparatus user friendly and painless for the patient, the clinician and any clinical personnel engaged in administering the ORIP treatment.

It is still another object of the invention to make ORIP treatment equally convenient in handling emergencies during the transport of the patient to the hospital as deployed in ischemic preconditioning of hospitalized patients prior to elective procedures. It is therefore also an object of the invention to provide a means to prevent multiple organ failures in critically ill patients admitted to the critical care/intensive care units It is yet another objective to provide a non-invasive device based procedure that accomplishes optimal pre-conditioning and pre-surgery preparation of the patient in approximately 20-25 minutes with a single touch, requiring little or no physician time and no discomfort or cumbersome routines of prior art to attend to.

It is yet another object of the invention to make ORIP treatment easily deployable across the board in any pre-intervention settings, whether revascularization of coronary arteries or organ transplant or protracted surgeries involving interruption of blood supply to organs during the course of the procedure. It is further object of the invention to reduce myocardial ischemic injury during angioplasty or bypass surgery. It is still further object of the invention to reduce the size of myocardial infarction, preserve the global systolic and diastolic function, and protect against arrhythmia during the reperfusion phase. It is also an object of the invention to provide a means of managing chronic conditions such as long term treatment of coronary artery disease by reducing the risk of major cardiovascular events which include myocardial infarction and stroke, and non-lethal cardiovascular symptoms which include angina pectoris and hypertension. It is yet further object of the invention to boost neocardiogenesis in patients undergoing protein, gene or stem cell therapy for growing natural vessels for bypassing the coronary blockages and repairing the damaged myocardium.

The instant invention meets these objectives by providing the optimal remote ischemic preconditioning (ORIP) system that uses two cuffs at two different anatomical locations (both upper limbs or both lower limbs or one upper and one lower limb etc.), which alternately inflate and deflate rendering ischemic stimuli to a march larger volume of the body in half the time and least patient discomfort. Both cuffs are synchronized by a single controlling console. This results in a more potent preconditioning response in a much shorter time. Moreover, the networkability of the ORIP system of the instant invention provides a means for real time interaction with the clinician who prescribed the ORIP treatment, and also with the patient if the treatment is prescribed for a long time.

Accordingly, the present invention is directed to devices, systems, methods, programs, computer products, computer readable media, software algorithms and other hardware components such as pneumatic cuffs, air pumps, valves, transducers and modules for controlling one or more operating parameters and components of the ORIP apparatus by either an attending clinician or remotely by a clinician not in attendance by sending and receiving programming from a remote server or system, such as the Web interface. The invention is equally well suited to user friendly self-administration of ORIP treatment by a chronically ill patient, as much as it useful in an emergency situation by paramedic administration of the treatment at a location remote from the hospital or clinic.

These advantages in addition to other objects and advantages of the invention will be set forth in the description which follows, and may be learned by the practice of the invention. The objects and advantages of the invention may be realized and obtained by means of the software, algorithms, devices, remote servers and combinations thereof particularly pointed out in the appended claims.

BRIEF DESCRIPTION OF THE DRAWINGS

FIG. 1. An illustration of an ORIP treatment session in progress.

FIG. 2. Block diagram of the elements ORIP apparatus and each of the pneumatic cuffs.

FIG. 3. Sequence of equal & alternating inflation/deflation cycles in left and right limbs.

FIG. 4. Sequence of escalating timing of inflation/deflation cycles in left and right limbs.

FIG. 5. ORIP EMS/P3/CC web architecture in an acute treatment scenario.

FIG. 6. Schematic representation ORIP apparatus with RF Module.

FIG. 7. ORIP web architecture in an acute/sub-acute treatment scenario.

FIG. 8. Illustration of ischemic zones in different embodiments of ORIP.

DETAILED DESCRIPTION OF THE INVENTION

It is advantageous to define several terms before describing the invention. It should be appreciated that the following terms are used throughout this application. Where the definition of terms departs from the commonly used meaning of the term, applicant intends to utilize the definitions provided below, unless specifically indicated. For the purpose of describing the instant invention following definitions of the technical terms are stipulated:

Ischemia: Ischemia, also spelt as ischaemia, is described as an inadequate flow of blood to a part of the body, caused by constriction or blockage of the blood vessels supplying it.

Angina Pectoris: Angina pectoris is the medical term for chest pain or discomfort due to coronary heart disease. Angina is a symptom of a condition called myocardial ischemia. It occurs when the heart muscle (myocardium) doesn't get as much blood (hence as much oxygen) as it needs. This usually happens because one or more of the heart's arteries (coronary blood vessels that supply blood to the heart muscle) is narrowed or blocked.

Endothelial Dysfunction: It is a systemic pathological state of the endothelium (the inner lining of our blood vessels) and can be broadly defined as an imbalance between vasodilating and vasoconstricting substances produced by (or acting on) the endothelium. Normal functions of endothelial cells include mediation of coagulation, platelet adhesion, immune function, nitric oxide (NO) bioavailability, control of volume and electrolyte content of the intravascular and extravascular spaces. Endothelial dysfunction can result from and/or contribute to several disease processes, as occurs in septic shock, hypertension, hypercholesterolemia, diabetes as well from environmental factors, such as from smoking tobacco products and exposure to air pollution.

ORIP: An Optimal Remote Ischemic Preconditioning method and apparatus for non-invasively inducing transient, repetitive and alternating ischemia and reperfusion of at least a pair of remote organs in a treatment regimen that renders maximal systemic protection to one or more of other targeted body organs of a patient in minimal possible dosing time or discomfort to the patient, either against acute injury caused by reperfusion of the target organ(s) after prolonged ischemia, or for increasing the threshold of organs to withstand acute or chronic physiological and pathological insults resulting therein in improvement of vascular functions of malfunctioning target organs. The physiological and therapeutic effects of ORIP is based on the ubiquitous endogenous protective mechanism of ischemic preconditioning explicitly seen at the cellular level in organs such as heart, brain, liver, kidney, gastrointestinal tract, pancreas, skeletal tissue and urinary bladder. (D M Yellon and J M Downey, Physiol Rev 83 (2003) 1113-1151). In fact, this phenomenon is universally present in all living tissue from bone marrow to skin and hair.

Prescription: Prescription conventionally implies a written instruction by a qualified medical practitioner to pharmacist to dispense specific medication, and to a patient to intake that specific drug or drugs, in specified doses, for a specified length of time. A prescription largely implies a pharmaceutical intervention. However within the meaning of the instant invention, prescription refers to prescribing non-pharmaceutical intervention that deploys regimented and device-measurable lifestyle alterations that include physical activity and behavioral changes involving habits and diets. It not only includes the prescription for treatment but also a prescription for prevention and rehabilitation. Rx is an abbreviation for prescription and usually precedes the description of the treatment advised by the clinician.

Ischemia Triggered Cellular Modulators (ITCMs): Arterial occlusion causing ischemia results in lack of oxygen (hypoxia) in the tissue inducing intracellular kinases and changes in mitochondrial function brought about by a cascade of cellul modulators produced locally and circulated systemically to extend the protective effect to all the organs of body. Oxygen gradients in cells are critical signals in modulation of a range of different physiological processes, such as development, stress, wound healing, inflammation etc. Initiating physiological response for maintaining the metabolic homeostasis is a function that eukaryotic cells undertake by sensing changes in local oxygen tension. It also results in increase in vasoactive metabolites such as adenosine and prostaglandins in the tissues downstream from the occlusion. Reduction in oxygen tension in the vascular smooth muscle cells surrounding the arterioles causes relaxation and dilation of the arterioles and thereby decreases vascular resistance. The beneficial effects of transient intermittent ischemia or hypoxia although much studied in myocardial tissue are now known to extend to all the remote organs of the body. These systemic beneficial effects are on account of a very long list of ischemia triggered cellular mediators (ITCMs), such as HIF, PDGF, VEGF, FGF, Interleukin 10, NF-Kappa B & TNF Alpha inhibiters, etc. to name just a few, released into circulation as a result of hypoxia induced in a remote organ. Through several complex signaling pathways these ITCMs have a positive impact on reducing energy requirements, altering energy metabolism, improving endothelial function, reducing inflammation, improving electrolyte homeostasis, improving genetic expression and reorganization, improving reperfusion tolerance due to less reactive oxygen species, releasing activated neutrophils, reducing apoptosis and improving microcirculatory perfusion compared to a tissue which is not subjected ischemic preconditioning (Pasupathy S and Horner-Vanniasinkam S. Eur. J. Vasc. Endovasc. Surg. 29 (2) (2005) 106-15). Thus ischemic pre-conditioning triggers a wide range of cellular modulators (ITCMs) that circulate throughout the body carrying its therapeutic effects to all organs of the body. Depending on the specific effects of ITCMs on various organs and physiological processes this invention describes six different clinical conditions wherein the ORIP treatment can be optimally beneficial.

Reperfusion: The restoration of blood flow to an organ or tissue such as after a heart attack, an immediate goal is to quickly open blocked arteries and reperfuse the heart muscles. Early reperfusion minimizes the extent of heart muscle damage and preserves the pumping function of the heart.

Reperfusion Injury: The term ischemia-reperfusion injury or just reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

Neocardiogenesis: Neocardiogenesis is homeostatic regeneration, repair and renewal of sections of malfunctioning adult cardiovascular tissue by means of coronary angiogenesis (vasculogenesis) and cardiac myogenesis to improve myocardial perfusion, ventricular function and to restore physio-anatomical integrity of heart; such regeneration of new functional tissue resulting from self-renewal and differentiation of, either tissue resident progenitor cells or circulating stem cells, modulated by a plethora of transcriptional factors, genes, growth factors, receptors, extracellular matrix, signaling pathways, all responding to temporospatial cues. Ischemia is known to boost the activity of angiogenesis and myogenesis promoting proteins, genes and stem cells.

Heart Repair: Heart repair is a brand new concept evolved from the recent findings that growth of new coronary vasculature and new myocardium to replace damaged myocardium can be induced by certain growth promoting factors. Although there has been plenty of encouraging in vitro and animal data, no clinical trial has so far been successful in inducing neocardiogenesis to any significant level.

Angioplasty: also referred as Balloon Angioplasty or percutaneous transluminal coronary angioplasty (PTCA) is the technique of mechanically widening a narrowed or obstructed blood vessel typically as a result of atherosclerosis. An empty and collapsed balloon on a guide wire, known as a balloon catheter, is passed into the narrowed locations and then inflated to a fixed size using water pressures some 75 to 500 times normal blood pressure (6 to 20 atmospheres). The balloon crushes the fatty deposits, so opening up the blood vessel to improved flow, and the balloon is then collapsed and withdrawn.

Myocardial Infarction (MI): Commonly known as a heart attack, MI or acute myocardial infarction (AMI) is the interruption of blood supply to part of the heart, causing some heart cells to die.

Coronary Artery Bypass Surgery: Also known as coronary artery bypass graft (CABG) surgery or heart bypass or just bypass surgery is a surgical procedure performed to relieve angina and reduce the risk of death from coronary artery disease. Arteries or veins from elsewhere in the patient's body are grafted to the coronary arteries to bypass atherosclerotic narrowings and improve the blood supply to the coronary circulation supplying the myocardium (heart muscle). This surgery is usually performed with the heart stopped, necessitating the usage of cardiopulmonary bypass; techniques are available to perform CABG on a beating heart, so-called "off-pump" surgery.

Ambulatory Patient: The term "ambulatory patient" refers to all users of the method and device of the instant invention, who are not bedridden or with incapacitated mobility whether suffering from a chronic disease or otherwise healthy at risk of one or more morbidities.

RF Module: An RF Module within the meaning of the description of the instant invention is a hardware which is capable of either generating and transmitting high frequency radio waves or receiving and reading high frequency radio waves for the purpose of wireless communication or wireless data transfer between two or more devices. The RF (radiofrequency) transmitter is also called as RF transponder and the RF receiver is also called as RF transceiver/reader. Such RF Modules are integrated within the devices to establish wireless communicability between them. The high frequency radio waves deployed by such RF Modules for communicating with each other are usually within the 3 MHz to 30 MHz range. When RF Transceiver Module detects an RF Transponder Module in its vicinity, which usually ranges between 1 cm and 10 ft, it automatically initiates a communication link. Bluetooth is a common example of an RF module.

Elective Procedure: A surgical intervention that can be scheduled by the clinician at a time and day on a future date is referred as elective procedure within the meaning of the description of the instant invention.

Multiple Organ Dysfunction Syndrome (MODS): MODS is the presence of altered organ function in acutely ill patients such that homeostasis cannot be maintained without intervention. It usually involves two or more organ systems. The condition usually results from infection, injury (accident, surgery), hypoperfusion and hypermetabolism. The primary cause triggers an uncontrolled inflammatory response. In operative and non-operative patients sepsis is the most common cause. Sepsis may be present in absence of any infection and may result in septic shock. In one-third of the patients no primary focus can be found.

EMS—Emergency Medical Services
P3—Pre-Procedure Preparation
CC—Critical Care
CMS—Chronic Medical Services

THE EMBODIMENTS

The novel features of the non-pharmacological ORIP treatment of the instant invention can be deployed in many different ischemia-reperfusion injury prevention scenarios and in prevention or rehabilitation of acute or chronic physiological and pathological insults to organs in various disease conditions. In the following detailed description numerous specific details are set forth in order to provide a thorough understanding of the present invention. However, so as not to obscure the present invention, every minor detail may not be covered. Nevertheless, it will be understood by those skilled in the art that the present invention may be practiced without these specific details. Accordingly ORIP is a technology platform that can be adapted and implemented in a long list of clinical conditions.

Based on the design features, networkability of the ORIP apparatus and the physiological mechanism that triggers the cascade of ischemia triggered cellular modulators (ITCMs), the clinical utility of ORIP treatment can be classified as acute deployment, sub-acute deployment or chronic deployment. Acute deployment of the ORIP device treatment may usually require a single session and may be in an EMS setting or in an elective procedure pre-conditioning setting or in an intensive care setting. While sub-acute treatment regimen includes scenarios requiring a limited time repeated ORIP dosing sessions ranging from a few weeks to a few months. However, chronic treatment will be long term permanent or semi-permanent use of the device. Accordingly following are the major preferred embodiments of the ORIP treatment device of the instant invention:
  a) Emergency Medical Service (EMS): ORIP can be implemented as a fully portable EMS device during the transport of the patient to the hospital in an ambulance, or in an emergency room during patient preparation for any emergency procedure for minimizing ischemia-reperfusion injury. Such cases include patients of acute myocardial infarction, stroke, trauma, etc.
  b) Pre-Procedure Preparation (P-3): ORIP can be implemented as an in-hospital pre-procedure preparation device prior to any scheduled elective surgical procedure. Such elective procedures that carry a very high risk of ischemia-reperfusion injury include but not limited to heart bypass surgery, angioplasty, vascular surgeries, organ transplants, etc.
  c) Critical Care (CC): ORIP can be implemented in yet another acute setting in critical care medicine. Patients requiring critical care may require support for hemodynamic instability (hypertension/hypotension), airway or respiratory compromise (such as ventilator support), acute renal failure, potentially lethal cardiac arrhythmias, or the cumulative effects of multiple organ dysfunction syndrome (MODS). MODS is a very common complication seen in critical care and the cause of mortality in most patients brought to CC. MODS patients are acutely ill such that homeostasis cannot be maintained without intervention. It usually involves two or more organ systems. ORIP can afford protection against MODS in such critically ill patients. The treatment regimen in these cases may be like the EMS and P-3 protocols, but the treatment sessions may be repeated within 6 to 48 hours depending upon the condition of the patient.
  d) Chronic Medical Service (CMS): ORIP can also be implemented as a chronic care CMS device on a long term basis such as for management of coronary artery disease for reducing the risk of major cardiovascular events which include myocardial infarction and stroke, and non-lethal cardiovascular symptoms which include angina pectoris and hypertension.

Based on duration of use in treating the non-acute and non-chronic sub-acute clinical conditions the ORIP embodiments may be:
  a) an adjunct in maximizing myocardial salvage and preventing restenosis within 6 months of revascularization procedure, and,
  b) an adjunct in protein, gene and stem cell therapy for growing collateral coronary arteries and repair infarcted myocardium.

These embodiments are herein described and illustrated through self explanatory drawings in FIGS. 1 through 8. In a preferred embodiment the apparatus comprises of using a pair of pneumatic cuffs wrapped around each of the limbs, for example left upper limb 10a and right upper limb 10b. Alternatively the cuffs can be used on the wrist. These pneumatic cuffs are very similar to those used with self-inflating oscillometric sphygmomanometers. These easy to apply cuffs, which can be used on any of the upper and lower limb combinations, can either be used by a clinician or the patient himself/herself without any assistance by simply wrapping the cuffs around the patient's selected pair of limbs. Separate air tubing connect both the pneumatic cuffs to an ORIP Console 12 housing the mechanical as well electronic components that operate both the cuffs automatically inflating and deflating in accordance to a pre-defined algorithm protocol upon pressing the Start or ON Button 14 on the ORIP Console. A series of protocols may be permanently programmed in the ORIP Console providing as options for the user to choose a particular ORIP regimen, or can be delivered to the Console from a remote location as a prescription from a remote clinician. For such remote wireless connectivity the ORIP Console may incorporate a Communication Module which may be wired or wireless 28 (WCM).

It should be noted at this point that in the various wireless embodiments described herein, all client-server data transfer between the wired or wireless nodes is implemented either through the telecommunication network or the Internet, using protocols such as but not limited to WAP (Wireless Application Protocol) or HTTP or TCP/IP communication or SMPP (short message peer-to-peer protocol) to and from the ORIP Console's wireless communication module preferentially according to the availability of the 802.11 and cellular data channels.

When the Internet connectivity hardware is either not incorporated within the ORIP Device Console or when the Internet is not accessible, a peer to peer communication can also be established with another wireless communication device in the vicinity via radiofrequency (RF) transmission between the RF Modules embedded within the Console and the wireless communication device (FIG. 6). Such wireless communication device can be a mobile phone, a laptop computer or even a stationary communication terminal placed within the radiofrequency range of the ORIP Console. These wireless communication devices may in turn transfer the data received from the ORIP Console to the ORIP network via the Internet. If the ORIP device or such other wireless communication devices in the vicinity support multiple communication modes, communication is attempted first using a TCP/IP connection over open 802.11 channels, second using GPRS-enabled bulk or stream transfer, and finally SMS/MMS can be used as a fallback.

Each ORIP cycle comprises of simultaneous alternating phases in each limb such as:
  a) an ischemic phase wherein first of the two auto-inflatable pneumatic cuffs inflate to a cuff pressure that significantly exceeds beyond the systolic blood pressure to completely occlude blood flow to the patient's first remote organ 10a (left limb) for a pre-defined period that is not less than 1 minute and not more than 10 minutes, and,
  b) a reperfusion phase wherein second of the auto-inflatable pneumatic cuffs deflates to allow free flow of blood to second remote organ such as the right limb 10b for a pre-defined period, which may not be less than 1 minute and not more than 5 minutes.

A single ORIP session may comprise of not less than 2 and not more than 5 of either escalating/deescalating/unequally/equally timed phases of alternating cycles per limb, accomplishing twice the ischemic body area for optimal release of the therapeutic ITCMs in half the time required by a single cuff procedure thereby resulting in more potent effect in a much shorter time without significant pain or discomfort to the patient.

As illustrated schematically in FIG. 2 each cuff may have its own corresponding air pump, which comprise of an air pump 16 with an inflate valve 18 to allow and sustain inflation during the ischemic phase at a cuff pressure that is significantly above the systolic blood pressure, and a deflate valve 20 to deflate the cuff during the reperfusion phase such that when the first limb 10a is in ischemic phase the second limb 10b is in reperfusion phase. Each pump of the air pumping module is connected to its corresponding cuff through tube. A pressure transducer 22 for each cuff senses pressure oscillations in the artery by changes in the counter-pressure off the cuff thus measuring the cuff pressure during an ORIP session. The pressure transducer may use either an oscillometric, or a photoplethysmographic, or an ultrasonic, or a thermal or an infrared transduction method to measure the minimal blood flow occlusion pressure (systolic blood pressure) to set up the maximal occlusion pressure (10-30% higher than systolic pressure) in the ischemic phase for each of the cuffs.

In addition to these hardware components for each cuff, there is a Microprocessor 24 that controls and operates both the cuffs 10a and 10b, and a Display 26 that provides user interface to start, monitor and review the ORIP data, display in a real time graphic user interface the ORIP treatment protocol, the status, interact with the clinician, receive treatment reminders, review the prognosis of the treatment and provide the user means controls and switch to start or stop device. The microprocessor is either pre-programmed or programmable to automatically inflate and deflate the pneumatic cuffs alternatively in predefined repetitive cycles in predefined order of each of the two remote organs (limbs). The console display and controls provide graphic user interface for real time user interaction with the microprocessor and other components that are stored in the microprocessor's memory bay which may include but are not limited to the selection and initiation of a particular ORIP session, calling for a readout of some previously stored data or the like, or setting into the microprocessor patient related data, as well as times and dates relating to specific ORIP sessions and regimen.

In FIG. 1, the upper arms 10a and 10b of a human subject are shown wearing automatic flexible inflatable and deflatable cuff for occluding the brachial artery when inflated beyond the subject's systolic blood pressure. Systolic pressure is the maximum arterial pressure that is produced during contraction of the left ventricle of the heart. A typical ORIP session begins when the user uses the ORIP Console Start/On button 14 to first select the specific ORIP regimen and then begin the process of inflating the pneumatic cuff. The Console Microprocessor 24 either utilizes a predefined target of inflation pressure or actually measures the systolic blood pressure to estimate the target inflation pressure in each cuff. Such target inflation pressure when predefined is not less than 200 mm Hg, and when it is estimated, it is not less than 10% and not more than 30% above systolic pressure in upper arm or wrist; and not less than 210 mm Hg, or not less than 10% and not more than 30% above systolic pressure in thigh. The Microprocessor retrieves the user selected ORIP regimen from its memory and initiates the ORIP session by inflating the first pneumatic cuff to a pressure that is 10-30% greater than the highest expected systolic reading using the oscillometric method. When the oscillations cease the maximum systolic pressure is reached. An ischemic zone is created distal to the inflated cuff. These ischemic zones are illustrated in each of the FIGS. 1, 5, 6, 7 and 8 by shaded areas. The preferred remote organs for administering the ORIP treatment regimen are but not limited to the extremities, more preferably the upper arm of the upper limbs and thigh of the lower limbs. For an ORIP session either both cuffs can be applied to upper arms of upper limbs, or to wrists, or to thighs of lower limbs or a combination of upper and lower limbs. As illustrated in FIG. 8, a right upper arm cuff 10b can be paired with a right thigh 10c, or left upper arm cuff 10a can be paired with right thigh 10c, or the cuffs can be applied to each of the right 10c and left thighs 10d. As can be inferred from FIG. 8 larger ischemic zones can be created with thigh cuffs as compared to upper arm cuffs as a much larger tissue mass is exposed to the ischemic effect in legs than in arms. As represented by the shaded areas FIG. 8 the ischemic zones created in lower limbs are larger than those created in upper limbs. Accordingly, the cycles of ischemic and reperfusion phases in an ORIP session can be further varied depending upon the remote organs selected for dosing.

The ORIP Console housing may also incorporate a Wireless Communication Module 28 to receive and send feeds from and to the clinician regarding the compliance to the clinician-prescribed ORIP treatment regimen, or to alter the ORIP treatment regimen, or to prescribe a new ORIP treatment regimen. The wireless communication module may use WIFI, GPRS, TCP/IP or a telecommunication protocol to transmit data to the Internet either directly (FIGS. 5 & 7) or use peer to peer RF transmission through an RF-enabled handheld communication device in the vicinity of the ORIP Console as illustrated in FIG. 6.

A graphic representation of the pressure in each of the two cuffs during ischemia and reperfusion cycles of a typical ORIP session is presented in FIGS. 3 and 4. In a preferred embodiment in FIG. 3 the ischemia and reperfusion phases are equal and alternating, meaning that when one cuff is inflated the other one is deflated. There is no overlap of the inflation and deflation cycles in this embodiment. However, in another preferred embodiment in FIG. 4 the ischemia/reperfusion cycles alternate at initiation of the first cycle but the inflation time escalates with subsequent inflation and there may be some overlapping of ischemic phase in respective limbs as the ORIP session continues because the deflation time remains constant in each limb. In gradually increasing the duration of the ischemic phase, the pre-conditioning effect may be more attuned to the natural physiological response to the ischemic episodes.

FIG. 5 illustrates an embodiment in which the ORIP apparatus is deployed in an acute EMS (emergency medical service) or P3 (pre-procedure preconditioning) or CC (Critical Care) setting in which ORIP regimen comprise of a single ORIP session of not less than 2 and not more than 5 ischemia/reperfusion cycles, except in CC, wherein repeat sessions may be warranted depending on the condition of the patient. FIG. 6 also illustrates the networkability of the ORIP apparatus, although it will be understood by those skilled in the relevant art that the ORIP treatment in EMS, P3 and CC settings can be administered even if the ORIP apparatus is not networkable. As described previously the ORIP Console 14 may incorporate within its housing a wireless communication module 28 to connect to a remote server 30, which enables Internet connectivity using any of the Internet connectivity protocols known to the prior art, such as WIFI, GPRS, TCP/IP or a telecommunication protocol to transmit data to the Internet either directly or using peer to peer RF transmission through an RF-enabled communication device 32 in the vicinity of the ORIP Console as illustrated in FIG. 6. Such RF-enabled communication device may be a mobile phone, a laptop or any computer connected to the internet. The ORIP data, whether stored or real time, can be accessed through Web interfaces designed for the Administrator 34, the Clinician 36 and the patient 38 mostly in sub-acute or chronic treatment settings, wherein, because of its networkability, the apparatus can be also be implemented even with a single cuff.

Examples of ORIP Clinical Applications: The benefits of the ORIP treatment can extend to any organ such as heart, lungs, brain, liver, kidneys, pancreas, intestines, urinary bladder, and all smooth and skeletal muscles and vasculature in general. The therapy can comprise of a standalone treatment for organ protection, or it can be used as an adjunct to an organ-protecting pharmacological agent for boosting the pharmacological agent's organ-protecting properties.

Following are six examples of how the preferred embodiments of ORIP can be deployed in treatment of different clinical conditions grouped under these six categories. These examples are only broadly illustrative of the scope of the novelty of the invention disclosed, and do not limit the utility of the ORIP procedure in any physiological or pathological condition where the organs and the vasculature is at risk of injury or compromised function on account of sub-optimal regulation of cellular mediators of injury, inflammation, tissue metabolism, vascular functions and tissue rebuilding, etc.

1. EMS (Emergency Medical Services): Heart attack or myocardial infarction is the leading cause for a good number of patients rushed to the hospital emergency room. These patients need angioplasty procedure immediately to open up the blocked artery that caused the myocardial infarction. Opening up the blocked artery restores the blood supply to the myocardium thereby limiting the damage to the myocardium. However, sudden reperfusion itself causes further damage to the myocardium because the well know ischemia-reperfusion injury phenomenon. It has been shown that if remote ischemic reperfusion is performed while the patient is on the way to the hospital, it reduces the extent of such ischemia reperfusion injury and salvages a larger portion of myocardium than it would be possible with the revascularization procedure itself. The ORIP method of the instant invention accomplishes the remote ischemic preconditioning in just 20-25 minutes automatically with one push on the start button and without continuously engaging a clinician in process that may take up to an hour without the ORIP device. ORIP EMS treatment can be completed in a single session comprising of not less than 1 minute and not more than 10 minutes each of the ischemia and reperfusion phases. At least 2 and not more than 5 of equally timed phases of such ischemia and reperfusion cycles per limb are administered in a single session. Alternatively the session may comprise of at least 2 and not more than 5 increasingly timed phases of ischemia cycles may be administered per limb. In either way the entire ORIP treatment can thus be accomplished during the time patient is placed on a stretcher, into the ambulance and brought into the hospital.

2. P3 (Pre-Procedure Preconditioning): Certain high ischemic-reperfusion injury risk procedures such as angioplasty, heart bypass, organ transplants, vascular surgeries are performed on an elective basis. These procedures are schedule ahead of time. ORIP treatment can be applied with the same convenience of short treatment administration time, maximal ischemic dosing, patient comfort, and single touch command without clinician supervision. The single session ORIP is administered in the same way as described in the EMS scenario.

3. CC (Critical Care): Critical care medicine is another setting wherein ORIP can be implemented. Patients requiring critical care may require support for hemodynamic instability (hypertension/hypotension), airway or respiratory compromise (such as ventilator support), acute renal failure, potentially lethal cardiac arrhythmias, or the cumulative effects of multiple organ dysfunction syndrome (MODS). MODS is a very common complication seen in critical care and the cause of mortality in most patients brought to CC. MODS patients are acutely ill such that homeostasis cannot be maintained without intervention. It usually involves two or more organ systems. ORIP can afford protection against MODS ORIP can afford protection against MODS in such critically ill patients by increasing the plasma levels of ITCMs which play a very important role in reducing energy requirements, altering energy metabolism, improving endothelial function, reducing inflammation, improving electrolyte homeostasis, improving genetic expression and reorganization, improving reperfusion tolerance due to less reactive oxygen species, releasing activated neutrophils, reducing apoptosis and improving microcirculatory perfusion, all of which protect the organs from any impending dysfunction in a critically ill patient. The treatment regimen in these cases may be similar to the EMS and P-3 protocols, but the treatment sessions may be repeated every 6, 12, 24 or 36 or 48 hours depending upon the condition of the patient.

4. CMS (Chronic Medical Service): ORIP can also be deployed in long term treatment of chronic diseases. Clinicians can prescribe ORIP therapy particularly in management of cardiovascular diseases such as coronary artery disease. Ischemic preconditioning has been shown to afford protection against endothelial dysfunction and reduce the extent of myocardial infarction (Kharbanda R K, et al. Circulation, 2002; 106: 2881-2883). Endothelial dysfunction is known to have profound effect on blood vessel elasticity, blood pressure and overall cardiovascular health. A key and quantifiable feature of endothelial dysfunction is the inability of arteries and arterioles to dilate fully in response to an appropriate stimulus that stimulates release of vasodilators from the endothelium like nitric oxide (NO). Endothelial dysfunction is commonly associated with decreased NO bioavailability, which is due to impaired NO production by the endothelium and/or increased inactivation of NO by reactive oxygen species. Decreased NO bioavailability not only cause hypertension but precipitates angina pectoris in patients of coronary artery disease. Oxygen gradients in cells are critical signals in modulation of a range of different physiological processes, such as development, stress, wound healing, inflammation etc. Initiating physiological response for maintaining the metabolic homeostasis is a function that cells undertake by sensing changes in local oxygen tension. ORIP treatment therefore not only can control hypertension and reduce episodes of angina pectoris, but can reduce the long term risk of major cardiovascular events such as myocardial infarction and stroke. Furthermore its collective impact on vasculature, inflammation, wound healing, free radical scavenging and increased capillary density, ORIP can also be used for treating patients of Raynaud's syndrome, peripheral arterial disease, diabetes, pulmonary hypertension, connective tissue disorders, and other chronic diseases involving the vasculature.

ORIP treatment regimen in chronic cases comprise of not less than 2 sessions per week and not more than 14 sessions per week, and each session comprising of not less than 2 and not more than 5 ischemic phases per limb, and not less than 2 and not more than 5 reperfusion phases per limb, each of the ischemic and reperfusion phases comprising of not less than 1 minute and not more than 10 minutes of ischemia and reperfusion respectively. As cardiovascular diseases are chronic, the ORIP treatment can continue lifelong if necessary.

5. Coronary Revascularization Adjunct: Prognosis in angioplasty/heart bypass procedures largely depends on the immediate and long term effects ischemia-reperfusion injury and actual physical trauma caused during the procedure. These injuries result in local inflammatory reaction which may result in restenosis. Because ORIP treatment reduces inflammation, improves endothelial function and improves free radical scavenging in addition to directly protecting from ischemia-reperfusion injury, it can have profound effect on the short and long term prognosis of revascularization in patients who undergo angioplasty/bypass procedures.

ORIP treatment regimen in patients undergoing angioplasty or heart bypass can be prescribed by the clinician as adjunct to coronary revascularization procedure and comprise of two phases:

a) An acute phase ORIP treatment consisting of a single session minutes or hours prior to the revascularization procedure whether bypass surgery or angioplasty, such session comprising of not less than 2 and not more than 5 ischemic phases per limb, and not less than 2 and not more than 5 reperfusion phases per limb, each of the ischemic and reperfusion phases comprising of not less than 1 minute and not more than 10 minutes of ischemia and reperfusion respectively.

b) A sub-acute phase ORIP treatment regimen initiated not earlier than the $3^{rd}$ day subsequent to the revascularization procedure whether bypass surgery or angioplasty, and continuing until 6 months post-procedure. such regimen comprising of not less than 2 sessions per week and not more than 14 sessions per week, and each session comprising of not less than 2 and not more than 5 ischemic phases per limb, and not less than 2 and not more than 5 reperfusion phases per limb, each of the ischemic and reperfusion phases comprising of not less than 1 minute and not more than 10 minutes of ischemia and reperfusion respectively.

6. Heart Repair Adjunct Many attempts to grow natural vessels and new myocardium to bypass blocked arteries and replace damaged heart tissue have been made but all of them have so far failed. This is because both angiogenesis and myogenesis components of neocardiogenesis can only be promoted in presence of a complex cascade of Ischemia Triggered Cellular Modulators (ITCMs). The under trial protein, gene or stem cell therapies administered to these patients can only function when there are sustained levels of ITCMs in the tissue for at least 8-12 weeks during which the new tissue is morphed. However, paradoxically after administering a single dose of these heart repair agents the patients are never exposed to ITCMs, because neither the patients that enter angiogenesis/heart repair trials can be kept away from their coronary vasodilators, nor other cardio-protective drugs they have been taking to maintain adequate myocardial perfusion be withdrawn. So the result is although they may have quite severe disease their heart is still not subjected to sufficient ischemia or adequate tissue levels of ITCMs to trigger growth of the new vessels or myocardium. ORIP can induce sustained optimal levels of ITCMs to boost the effect of the heart repair agents resulting in generation of new vessels and renew myocardium in patients of coronary artery disease. In these scenarios ORIP can be prescribed by the clinician as adjunct to protein, gene or stem cell therapy for inducing neocardiogenesis for growing natural vessels for bypassing the coronary blockages and repairing the damaged myocardium. As in coronary revascularization treatment already discussed previously the treatment comprises of:

a) An acute phase ORIP treatment consisting of a single session similar to the one described in adjunctive treatment in coronary revascularization procedures b) A sub-acute phase ORIP treatment regimen similar to the already described in adjunctive treatment in coronary revascularization except that the treatment continues for at least 8-12 weeks post-procedure until which time the coronary collaterals are expected to grow.

The description of the present invention has been presented for purposes of illustration and description, and is not intended to be exhaustive or limited only to the novelty in the form disclosed. Many modifications and variations as suited to any specific use contemplated will be apparent to those of ordinary skill in the art.

What I claim as my invention:

1. An Optimal Remote Ischemic Preconditioning (ORIP) method for non-invasively inducing transient, repetitive and alternating ischemia and reperfusion of at least a pair of remote organs including a first limb and a second contralateral limb in a treatment regimen that renders maximal systemic protection to one or more of other targeted body organs of a patient in minimal possible dosing time and patient discomfort, either against acute injury caused by reperfusion of the target organ(s) after prolonged ischemia, or for increasing the threshold of the target organs to withstand acute or chronic physiological and pathological insults resulting therein in release of ischemia triggered cellular modulators (ITCMs) optimally that cause improvement of physiological functions of malfunctioning target organs comprising the steps of:

a) Providing a pair of auto-inflatable pneumatic cuffs, attaching a first cuff to the first limb and a second cuff to the second limb, wherein one of the cuffs inflates significantly beyond systolic blood pressure to completely occlude the blood flow in ischemic phase, and deflate one of the contralateral paired cuffs to allow free flow of blood in the contralateral limb in reperfusion phase, wherein inflation and deflation in the paired cuffs is done in cycles that alternate with similar but opposite ischemia-reperfusion cycles of the paired cuff attached to the patient's remote organs resulting in systemic release of optimal levels of therapeutic ITCMs;

b) Providing an air pumping module with a single or paired air pump, an inflate and a deflate valve for each of the paired cuffs, which pump air to each cuff through a tube and holds air in the ischemic phase at a cuff pressure significantly beyond the systolic blood pressure for occluding the blood flow to the patient's first remote organ for a predefined time, and releases the air in the reperfusion phase allowing the blood to flow freely, thereby when the first organ is in ischemic phase the second organ is in reperfusion phase, resulting in accomplishing twice the ischemic body area for the release of the therapeutic ITCMs in half the time required by a single cuff ischemic preconditioning procedure and thus providing a more potent therapeutic effect without causing significant patient discomfort;

c) Providing a pressure transducer module for measuring the minimal blood flow occlusion pressure to set up the maximal occlusion pressure in the ischemic phase for each of the paired cuffs, wherein the transducer is selected from the group consisting of: an oscillometric transducer, a photoplethysmographic transducer, an ultrasonic transducer, a thermal transducer, or an infrared transducer;

d) Providing a controller console housing which has mechanical and electronic components that automatically operate both the paired, the air pumping module, the transducers, a user interface and a microprocessor that is programmable to automatically inflate and deflate the pneumatic cuffs alternatively to predefined cuff pressure levels, in predefined repetitive cycles, and in predefined order of each of the two remote organs, wherein the controller console displays the ORIP treatment protocol and the status in a real time graphic user interface for user interaction with the microprocessor and other electronic components that are stored in the microprocessor selected from the group consisting of: selection and initiation of a particular ORIP session in compliance with clinician's prescription, calling for a readout of some previously stored data, or setting into the microprocessor patient related data, times and dates relating to specific ORIP sessions and regimen, and also providing user with means to switch the device on or off; and e) Providing a wired or wireless communication module to receive and send feeds from and to a clinician regarding the compliance to a clinician-prescribed ORIP treatment regimen, to alter the ORIP treatment regimen, or to prescribe a new ORIP treatment regimen, wherein the wireless communication is selected from the group consisting of WIFI, GPRS, TCP/IP or peer to peer RF transmission through an RF-enabled handheld communication device in the vicinity of the ORIP console.

2. The method of claim 1 wherein:
a) the first remote organ comprises an upper arm or a wrist, wherein the highest occlusion pressure is set to not less than 10% and not more than 30% higher than the highest systolic blood pressure measured in the corresponding upper limb, or not more than 200 mm Hg when the systolic upper limb pressure is not measured by the device; or
b) the first remote organ comprises a lower limb like a thigh in which case the highest occlusion pressure is set to not less than 10% and not more than 30% higher than the highest systolic blood pressure measured in the corresponding thigh, or not more than 210 mm Hg when the systolic thigh pressure is not measured by the device; or
c) the first remote organ comprises a combination of the upper and the lower limbs thereof at their corresponding occlusion pressures respectively.

3. The method of claim 1, wherein the organs targeted for the benefit of the ORIP treatments are heart, lungs, brain, liver, kidneys, pancreas, intestines, urinary bladder, and all smooth and skeletal muscles and vasculature in general, whether used as a standalone treatment for organ protection, or as an adjunct to an organ-protecting pharmacological agent for boosting the pharmacological agent's organ-protecting properties.

4. The method of claim 1, wherein the ORIP treatment regimen is completed in a single session comprising of not less than 1 minute and not more than 10 minutes of the ischemia phase and not less than 1 minute and not more than 5 minutes of reperfusion phase and implementing is a single session not less than 2 and not more than 5 each of either escalating or deescalating or unequally timed or equally timed phases of alternating cycles of ischemia and reperfusion per limb, wherein the ORIP treatment can be performed:
a) as emergency medical service (EMS) device while the patient is being transported to the hospital for an emergency medical intervention in myocardial infarction, cerebral stroke, or, trauma or,
b) as a pre-procedure preparation (P3) device prior to an elective intervention selected from the group consisting of: a coronary bypass surgery, a coronary angioplasty, a vascular surgery, or an organ transplant or,
c) as a critical care (CC) device for prevention of multiple organ dysfunction syndrome (MODS), in which case the ORIP treatment session may be repeated in not less than 6 hours and not more than 48 hours as long as the patient remains in the critical care.

5. The method of claim 1, wherein the ORIP is provided as a chronic medical service (CMS) for treatment of chronic cardiovascular diseases prescribed by the clinician to be administered on a long term basis for management of coronary artery disease by affording protection against endothelial dysfunction and reducing the risk of major cardiovascular events which include myocardial infarction and stroke, and non-lethal cardiovascular symptoms which include angina pectoris and hypertension, comprising of not less than 2 sessions per week and not more than 14 sessions per week, and each session comprising of not less than 2 and not more than 5 ischemic phases per limb, and not less than 2 and not more than 5 reperfusion phases per limb, wherein each of the ischemic and reperfusion phases comprising of not less than 1 minute and not more than 10 minutes of either escalating or deescalating or unequally timed or equally timed alternating cycles of ischemia and reperfusion respectively.

6. The method of claim 1, wherein a Web enabled patient interface is provided for patients to review ORIP prescription, follow up on ORIP treatment compliance, interact with the clinician, receive treatment reminders, and review prognosis of the treatment, using an Internet-enabled computer or handheld communication device.

7. The method of claim 1, wherein ORIP is prescribed by the clinician as adjunct to coronary revascularization procedure for not only preventing ischemia-reperfusion injury to the myocardium, but preventing post-procedure cardiovascular events including restenosis (re-blockage) of the coronary arteries, the treatment comprising the steps of:
a) Providing an acute phase ORIP treatment consisting of a single session minutes or hours prior to the revascularization procedure whether bypass surgery or angioplasty, wherein the session comprises of not less than 2 and not more than 5 ischemic phases per limb, and not less than 2 and not more than 5 reperfusion phases per limb, each of the ischemic and reperfusion phases comprising of not less than 1 minute and not more than 10 minutes of ischemia and reperfusion respectively; and
b) Providing a sub-acute phase ORIP treatment regimen initiated not earlier than the 3.sup.rd day subsequent to the revascularization procedure whether bypass surgery or angioplasty, and continuing until 6 months post-procedure, such regimen comprising of not less than 2 sessions per week and not more than 14 sessions per week, and each session comprising of not less than 2 and not more than 5 ischemic phases per limb, and not less than 2 and not more than 5 reperfusion phases per limb, each of the ischemic and reperfusion phases comprising of not less than 1 minute and not more than 10 minutes of alternating ischemia and reperfusion cycles respectively.

8. The method of claim 1, wherein ORIP is prescribed by the clinician as adjunct to protein, gene or stem cell therapy for inducing neocardiogenesis for growing natural vessels for bypassing the coronary blockages and repairing the damaged myocardium, the treatment comprising the steps of:
a) Providing an acute phase ORIP treatment consisting of a single session minutes or hours prior to the administration of the protein, gene, or stem cell to the heart tissue, wherein the session comprising of not less than 2 and not more than 5 ischemic phases per limb, and not less than 2 and not more than 5 reperfusion phases per limb, each of the ischemia and reperfusion phases comprising of not less than 1 minute and not more than 10 minutes of ischemia and reperfusion respectively; and
b) Providing a sub-acute phase ORIP treatment regimen initiated not earlier than the 3.sup.rd day subsequent to the administration of the protein, gene, or stem cell to the heart tissue, and continuing until at least 8-12 weeks post-procedure, such regimen comprising of not less than 2 sessions per week and not more than 14 sessions per week, and each session comprising of not less than 2 and not more than 5 ischemic phases per limb, and not less than 2 and not more than 5 reperfusion phases per limb, each of the ischemic and reperfusion phases comprising of not less than 1 minute and not more than 10 minutes of alternating ischemia and reperfusion cycles respectively.

* * * * *